United States Patent [19]

Kay

[11] 4,084,442
[45] Apr. 18, 1978

[54] CONTROL OF PROCESSES

[75] Inventor: David Kay, Castle Donnington, England

[73] Assignee: The Boots Company Limited, England

[21] Appl. No.: 744,895

[22] Filed: Nov. 24, 1976

[30] Foreign Application Priority Data

Nov. 27, 1975 United Kingdom ............... 48907/75

[51] Int. Cl.² .................................... G01N 15/00
[52] U.S. Cl. ............................................. 73/432 PS
[58] Field of Search ..................... 73/432 R, 432 PS; 340/236; 241/36

[56] References Cited

U.S. PATENT DOCUMENTS

| 3,340,733 | 9/1967 | Lasher | 73/228 |
| 3,654,075 | 4/1972 | Keyes et al. | 241/36 |

FOREIGN PATENT DOCUMENTS 920,218  3/1963  United Kingdom ................ 340/236

Primary Examiner—Anthony V. Ciarlante
Attorney, Agent, or Firm—Lawrence Rosen; E. Janet Berry

[57] ABSTRACT

The end-point of an operation in which the flow properties of particulate material are altered during agitation is determined using a probe inserted into the vessel in which agitation occurs and which deflects when hit by material being agitated and detecting when the amplitude and/or frequency of the deflections of the probe changes to a given level.

11 Claims, 2 Drawing Figures

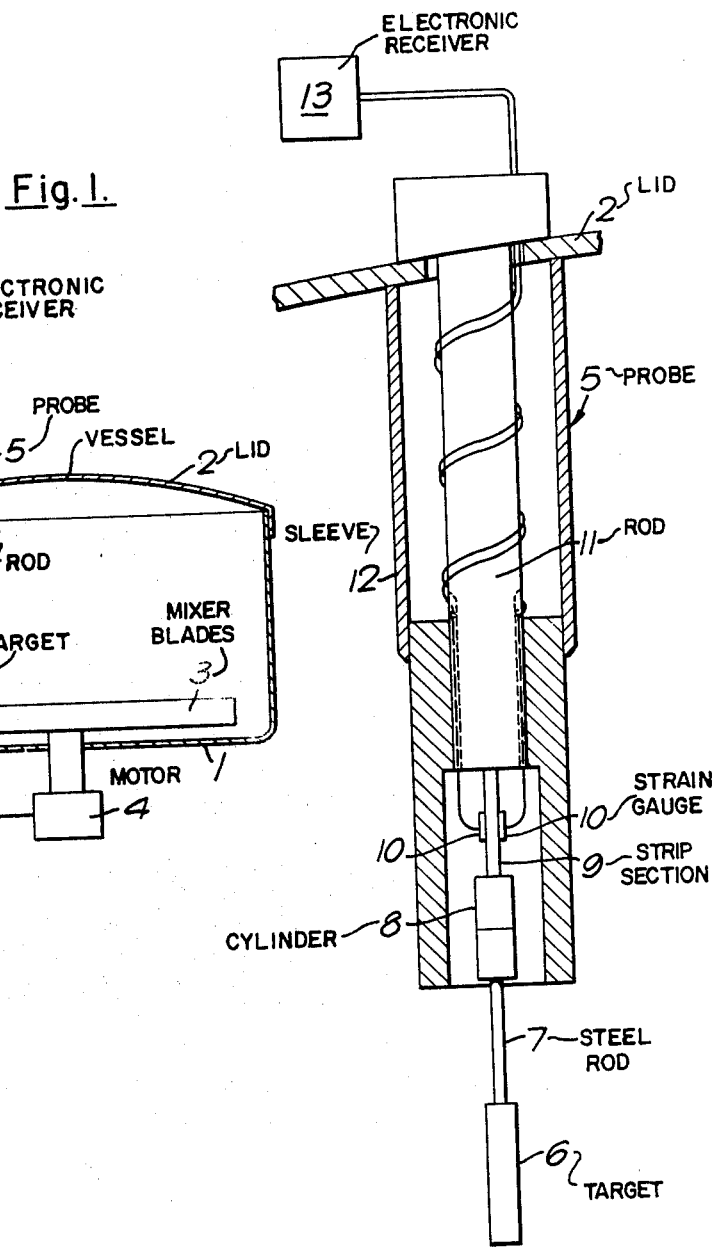

CONTROL OF PROCESSES

This invention relates to methods of control of processes in which particulate materials are agitated.

During various processes in which particulate materials are agitated a change in flow properties of the material may occur. It is often important that the agitation is stopped when the flow properties have altered to a desired degree.

Thus, for example when tabletting powders, e.g. to form tablets containing medicaments, it is usually necessary to granulate the powder to a desired degree before the material is compressed into tablets. This is usually done by mixing the powder, in the presence of granulating aids. It is important in any particular mixture that the correct degree of granulation is achieved. If the mixtures are granulated either insufficiently or by too much then unsatisfactory tablets will be formed.

One way of determining how the granulating is proceeding is to measure the electrical current used by the mixer, which increases due to the increased motor load as the mixture becomes more granulated. The mixing can then be stopped when the current reaches a predetermined level. However, this method of determining the "end-point" is not very accurate since the current fluctuates and variables occur due to energy losses in gear trains, bearings etc. It is thus easy to either go beyond the "end-point" and spoil a batch of material or to stop before the correct "end-point" has been reached, thus wasting time.

In another agitating operation, where "end-point" determination is important, tablet cores are coated with sugar by pouring sugar solution over them whilst being tumbled in a rotating pan. When the sugar solution has been dispersed over the surfaces of all the tablets hot air is blown over the tablets to dry them. In order to achieve maximum efficiency of pan use, it is desirable that the drying operation should be stopped as soon as possible after all the tablets are dried to the correct degree. Too much drying can also result in the the coating becoming brittle and some being lost by abrasion. To achieve the right amount of drying it is necessary to have an accurate "end-point" determination. Methods proposed have included determining the humidity of outgoing drying air, but this and other previous methods suffer from drawbacks.

We have now devised a simple method of determining such "end-points".

Thus according to the invention there is provided an apparatus for determining the end-point of an operation in which the flow properties of particulate material are altered during agitation which comprises a probe adapted to be inserted into the vessel in which agitation occurs and which deflects when hit by material being agitated and means for detecting when the amplitude and/or frequency of the deflections of the probe changes to a given level.

Generally the end-point that is being sought is when the amplitude of the deflections of the probe changes to a higher given level. However, in some operations the amplitude decreases as the operation proceeds, for instance, if the particles become generally smaller and the end-point of interest might therefore be when the amplitude of the deflections of the probe has decreased to a given level. Usually it is necessary for a number of deflections of the given amplitude to have been detected before the end-point is reached. However in some cases as soon as the given amplitude is detected the end-point is reached. Similarly, the amplitude of the vibrations may not always be critical but the end-point may occur merely when the frequency has changed to a given level.

However, the invention is particularly applicable for determining end-points where the frequency of the deflections of the probe above a given amplitude increases above a given level.

The preferred method of detecting the deflections is by means of a strain gauge attached to the probe whereby the amplitude of the deflection of the probe can easily be determined. Other methods include piezoelectric means or optical means.

The probe may conveniently comprise a narrow steel or brass rod having an enlarged "target" at its end. The strain gauge is usually attached to a narrow section of the rod.

Generally, there is also provided warning means and/or feedback means which are activated when the detecting means has detected that the amplitude and/or frequency of the deflections of the probe changes to a given level.

The probe may be attached to the vessel in which the agitation occurs or it may be attached to an external point, such as rigid frame and merely be inserted into the agitation vessel. When attached to the vessel this may be to any suitable position which would be apparent from the particular vessel and/or operation being carried out.

When granulating material to be tabletted, this is usually done in a machine similar to that used for dough making. In such a case the probe may conveniently be fixed to the lid of the machine so that it extends downwards into the mixing vessel. As the granulation proceeds the momentum of the particles changes and hence the amplitude of deflections induced in the probe, when it is hit by particles, also changes.

In some mixing machines it may be convenient to attach the probe to a wall of the vessel and, if necessary arrange for the mixer blades to be cut away so that the probe can be positioned through them as they rotate.

To determine the end-point of drying of coated tablets the probe may conveniently be mounted on a rigid frame in front of the drying pans and inserted into the tablets. As the pan rotates the tablets are tumbled and then roll back under gravity. As they become drier they move around more freely and their momentum increases and hence the amplitude of the deflections in the probe increases.

The warning means may comprise a light and/or sound alarm such as a bell or a siren, to alert the operator that the end-point has been reached. In the case of granulating powder the stirrer of the mixing machine will then be stopped to prevent any further granulation. In the case of drying tablets the operator will generally initially cut off the hot drying air and if necessary, will then add more sugar solution to provide a further coating to the tablet, which will then be dried again when the solution has been fully dispersed over the tablets. When the desired number of coatings has been applied the rotating pan can be stopped.

As well as or instead of the warning means, a feedback mechanism can be incorporated whereby the above operations can be carried out automatically. Thus when the end-point of the granulation is reached, the stirrer will be stopped automatically. Similarly, when coated tablets have been satisfactorily dried, the hot drying air may be cut off automatically and if desired, further sugar solution can be automatically added or the rotating pan can be stopped automatically.

The invention is illustrated in the accompanying drawings in which:

FIG. 1 is a elevation view of a granulating mixer with the probe in position, and FIG. 2 is an enlarged view of the probe.

Referring to the drawings, the mixer comprises a vessel 1 having a lid 2 and mixer blades 3 rotated by an electric motor 4. Attached to the lid is a probe 5, which comprises a cylindrical stainless steel target 6 connected via steel rod 7, to a brass cylinder 8 which narrows down to a strip section 9 to which are attached strain gauges 10. The brass section 9 is connected to a rigid stainless steel rod 11 which is fixed to the lid 2.

The upper portion of the probe is surrounded by a sleeve 12 which is also fixed to the lid. The lower part of the rod 11 fits tightly within the sleeve 12. Wires from the strain gauges 10 lead to an electronic receiver 13, which records the vibrations detected by the strain gauges 10 and is electrically connected to the stirrer motor 4 whereby when the frequency of the vibrations above a given amplitude increases above a given level, the motor automatically switches off.

When granulating a powder prior to being tabletted the powder, mixed with granulating aids, is sirred in the vessel 1 by the rotating mixer blades 3. When moving particles hit the target 6, the probe is deflected and the vibrations in the strip 9 are detected by the strain gauges 10. As the powder becomes more granulated the size and, hence the momentum, of the moving particles increases and the amplitude of the deflections of the probe increase.

The degree of granulation required will depend on the mixture to be tabletted. This is usually determined by trial and error.

When this point is achieved the desired amplitude of the deflections can be noted. The frequency of the vibrations above this amplitude can also be noted. The apparatus can then be programmed so that when the next batch of the same mixture is to be granulated, the mixer is stopped when that frequency of vibrations above the given amplitude is reached.

We have found for example that when granulating a mixture containing the drug, paracetamol, prior to tabletting, using the apparatus of the invention, and letting the machine shut off automatically, the degree of granulation does not vary from batch to batch. However, it has been found that when the machine is switched off, the motor current reading at that point varied by wide limits from batch to batch. Thus if the operator had switched off each time at the same predetermined current as is done conventionally, the degrees of granulation would have varied from batch to batch.

I claim:

1. An apparatus for determining the end-point of an operation in which the flow properties of particulate material are being altered during agitation comprising an agitation vessel provided with agitation means and a probe extending into the agitation vessel, said probe deflecting when hit by particulate material being agitated, and means for detecting when the amplitude and/or frequency of the deflections of the probe changes to a given level.

2. An apparatus according to claim 1 in which the agitation means is an internally disposed stirrer.

3. An apparatus according to claim 1 in which the deflections are detected by a strain gauge attached to the probe whereby the amplitude and the frequency of the deflections of the probe can be determined.

4. An apparatus according to claim 1 which also comprises warning means and/or feedback means which are activated when the detecting means has detected that the amplitude and/or frequency of the deflections of the probe have changed to a given level.

5. An apparatus according to claim 4 in which the feedback means operates to stop the agitating operation.

6. An apparatus according to claim 1 in which the detecting means comprise means for detecting when the frequency of the deflections of the probe above a given amplitude increases above a given level.

7. An apparatus according to claim 1 in which the agitation vessel is a mixing vessel for granulating a powder and wherein the probe is fixed to the lid of said vessel and extends downwards into said vessel which is also provided with internally disposed mixing means.

8. A method of determining the end-point of an operation in which the flow properties of particulate material are altered during agitation, which comprises agitating said particulate material in an agitation vessel provided with a probe extending into the agitation vessel and arranging for the probe to be hit by the particulate material while they are being agitated in said vessel thereby causing the probe to be deflected and detecting when the amplitude and/or frequency of the deflections of the probe changes to a given level.

9. A method according to claim 8 in which the deflections are detected by a strain gauge attached to the probe whereby the amplitude and the frequency of the deflections of the probe can be determined.

10. A method according to claim 8 in which the frequency of the deflections of the probe above a given amplitude are detected when they reach a given level.

11. A method according to claim 8 in which feedback means to alter the agitating operation are activated when the detecting means has detected that the amplitude and/or frequency of the deflections of the probe have changed to a given level.

* * * * *